United States Patent
Gordon

(10) Patent No.: US 7,291,175 B1
(45) Date of Patent: Nov. 6, 2007

(54) METATARSAL PHALANGEAL IMPLANT WITH LOCKING SCREW

(76) Inventor: David J Gordon, 303 Beverly Rd., apt. 8E, Brooklyn, NY (US) 11218

( * ) Notice: Subject to any disclaimer, the term of this patent is extended or adjusted under 35 U.S.C. 154(b) by 198 days.

(21) Appl. No.: 11/030,268

(22) Filed: Jan. 6, 2005

(51) Int. Cl.
*A61F 2/42* (2006.01)

(52) U.S. Cl. .................. 623/21.19; 623/21.11; 606/98

(58) Field of Classification Search .. 623/21.11–21.19; 606/98, 104
See application file for complete search history.

(56) References Cited

U.S. PATENT DOCUMENTS

| | | | |
|---|---|---|---|
| 3,506,982 A | 4/1970 | Steffee | |
| 4,156,296 A | 5/1979 | Johnson et al. | |
| 4,231,121 A * | 11/1980 | Lewis | ........... 623/21.16 |
| 4,642,122 A | 2/1987 | Steffee | |
| 4,908,031 A | 3/1990 | Frisch | |
| 5,037,440 A | 8/1991 | Koenig | |
| 5,207,682 A * | 5/1993 | Cripe | ........... 606/96 |
| 5,326,366 A | 7/1994 | Pascarella et al. | |
| 5,360,450 A | 11/1994 | Giannini | |
| 5,458,648 A | 10/1995 | Berman et al. | |
| 5,683,466 A | 11/1997 | Vitale | |
| 6,099,571 A | 8/2000 | Knapp | |

FOREIGN PATENT DOCUMENTS

| | | |
|---|---|---|
| FR | 2733412 | 10/1996 |
| WO | WO01/03613 | 1/2001 |

* cited by examiner

*Primary Examiner*—Bruce Snow
(74) *Attorney, Agent, or Firm*—Michael I Kroll

(57) ABSTRACT

A prosthetic metatarsal implant comprising a head and a neck extending from the head. A stem having at least one anchoring aperture extending transversely therethrough extends from the neck for insertion into a metatarsal bone. Means received by the at least one anchoring aperture for anchoring the stem in the metatarsal bone.

4 Claims, 9 Drawing Sheets

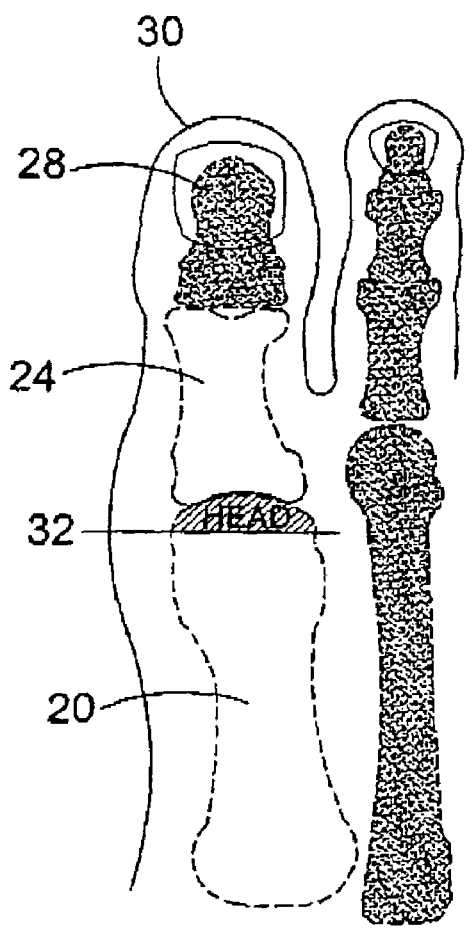
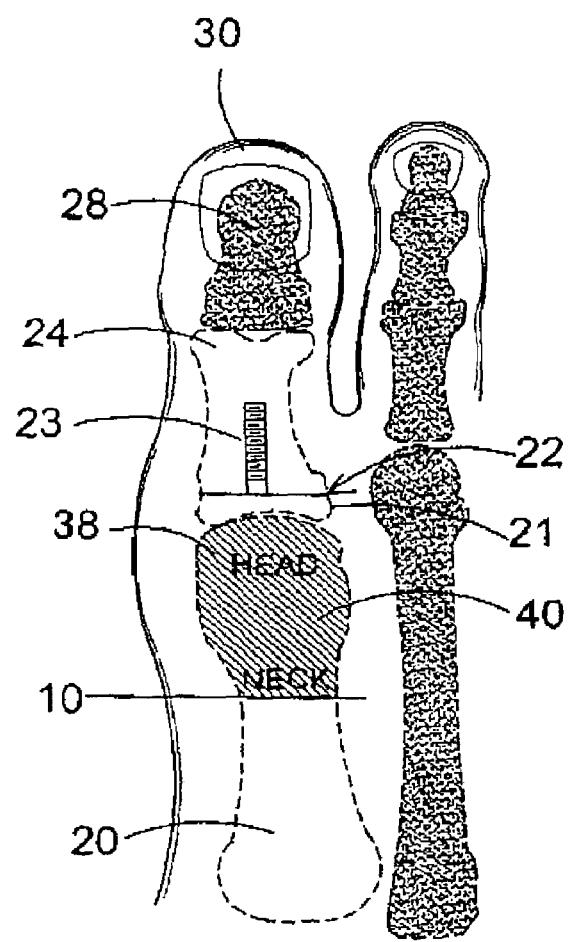
FIG. 2A
(PRIOR ART)
FIG. 2B
FIG. 2

METATARSAL PHALANGEAL IMPLANT WITH LOCKING SCREW

BACKGROUND OF THE INVENTION

1. Field of the Invention

The present invention relates generally to implants and, more specifically, to a metatarsal implant comprising a head and neck prosthesis anchored by an implant stem positioned within the remaining portion of the metatarsal bone and further secured by a pair of screws that pass substantially perpendicular through the implant stem at opposing quadrants.

The metatarsal implant also includes a cavity for inserting a targeting bracket having a post and cantilevered arm terminating in an annular ring. The targeting bracket allows for blind drilling of at least one hole for receipt of the transverse locking screws passing through the implant stem.

The phalanx component also includes a cavity for inserting a targeting bracket having a post and cantilevered arm terminating in an annular ring. The targeting bracket allows for blind drilling of at least one hole for receipt of the transverse locking screws passing through the implant stem.

2. Description of the Prior Art

There are other anchoring methods designed for implants. Typical of these is U.S. Pat. No. 3,506,982 issued to Steffee on Apr. 21, 1970.

Another patent was issued to Johnson et al. on May 29, 1979 as U.S. Pat. No. 4,156,296. Yet another U.S. Pat. No. 4,642,122 was issued to Steffee on Feb. 10, 1987 and still yet another was issued on Mar. 13, 1990 to Frisch as U.S. Pat. No. 4,908,031.

Another patent was issued to Koenig on Aug. 6, 1991 as U.S. Pat. No. 5,037,440. Yet another U.S. Pat. No. 5,326,366 was issued to Pascarella et al. on Jul. 5, 1994. Another was issued to Giannini on Nov. 1, 1994 as U.S. Pat. No. 5,360,450 and still yet another was issued on Oct. 17, 1995 to (Berman et al. as U.S. Pat. No. 5,458,648.

Another patent was issued to Vitale on Nov. 4, 1997 as U.S. Pat. No. 5,683,466. Yet another U.S. Pat. No. 6,099,571 was issued to Knapp on Aug. 8, 2000. Another was issued to Emmanuel on Jan. 18, 2001 as International Patent Application No. WO01/03613 and still yet another was issued on Oct. 31, 1996 to Huc de Bat as French Patent No. FR2733412.

U.S. Pat. No. 3,506,982

Inventor: Arthur D. Steffee

Issued: Apr. 21, 1970

An Implantable type endoprosthesis for ginglymus joints made of materials which are substantially inert when implanted in the body comprising, (a) a protuberant headed member comprising, (1) a stem portion for affixing said member in bone, (2) a neck portion on one end of said stem, and (3) a protuberant head portion on said neck portion; and (b) a socketed member comprising, (1) a stem portion for affixing said member in bone, and (2) a polymeric socket portion on one end of said stem and having wall portions defining the socket cavity with lip portions defining an elongated aperture communicating with said cavity, at least one of said lip portions being flexible, said protuberant head portion of said protuberant headed member removably retained in said socket cavity by said lips for cooperating angular motion, said neck portion locating in said elongated aperture, said elongated aperture being narrower than said protuberant head portion and approximately as wide as said neck portion over the greater portion of the length of said aperture so that the motion of said neck portion in said aperture is substantially limited to a single plane and said endoprosthesis approximates the motion of a natural ginglymus joint.

U.S. Pat. No. 4,156,296

Inventor: Kenneth A. Johnson et al.

Issued: May 29, 1979

An endoprosthetic device for a prosthesis between metatarsal and phalangeal bones comprising proximal and distal components which are engageable with each other. The proximal component has a convex, part-spherical bearing surface and a stem projecting from this surface for securing the proximal component into the end of the first metatarsal. The distal component has a concave, part-spherical bearing surface and a stem projecting from this surface for securing the distal component into the end of the phalanx adjacent to the first metatarsal. The engagement of the two components forms a less-than-hemispherical articulation.

U.S. Pat. No. 4,642,122

Inventor: Arthur D. Steffee

Issued: Feb. 10, 1987

An implantable joint for replacing a human toe joint. The joint includes a one-piece tack member implantable into the distal end of a metatarsal, and a one-piece socket member implantable into the proximal end of a phalanx. The tack member has an enlarged head defining a smooth part-spherical convex bearing surface which engages a smooth part-spherical concave bearing surface on an enlarged head of the socket member. The head of the socket member is elliptical in cross section so that the concave bearing surface extends through about 90 degrees in the vertical direction. The convex bearing surface of the tack member is nonsymmetrical relative to the longitudinal axis and extends through an angle which closely approximates 180 degrees, with this bearing surface projecting downwardly from the horizontal longitudinal axis through an extent greater than 90 degrees. Each of the members has a stem which projects for engagement within the respective bone, the stems being disposed with their longitudinal axes extending generally parallel with but disposed downwardly from the longitudinal axes of the respective head parts.

U.S. Pat. No. 4,908,031

Inventor: Eldon E. Frisch

Issued: Mar. 13, 1990

The invention provides an improved prosthetic toe joint adapted for replacement of a human toe joint which includes at least one one-piece member for implantation into the bone of the joint. The implant has a concave articulating surface which articulates against another one-piece component having a mating convex surface or against a mating convex bone surface. This one part component is provided with a flexible hinge section at the junction of its stem and the enlarged head portions. The hinge section is formed from a section of the stem which extends laterally outwardly on both sides of the stem portion adjacent the junction with the head. The laterally enlarged section is provided with a longitudinal channel extending through its midsection to form a hinge. Each of the one-piece components is preferably molded of a flexible elastomeric, physiologically inert material, for example medical grade silicone rubber.

U.S. Pat. No. 5,037,440

Inventor: Richard D. Koenig

Issued: Aug. 6, 1991

A prosthetic joint for replacing a metatarsal-phalangeal joint of a human toe has a head with a convex bearing surface that moves against the concave bearing surface of a base. The base is elliptical and formed by two different radii of curvature with a desired ratio. The head has a generally concave bone confronting surface with four different generally flat surface areas, one surface is horizontal and parallel to the longitudinal axis of the metatarsal bone, another extends approximately perpendicular thereto, and two others extend at angles to the longitudinal axis. The horizontal lower surface allows better distribution of vertical force and helps to resist separation of the head from the bone. The head exterior surface has four different regions formed by four different radii of curvature with desired ratios to one another. These four head surfaces allow the head and base to reproduce pivoting of a healthy toe joint. A method for installing the prosthetic joint is also disclosed.

U.S. Pat. No. 5,326,366

Inventor: Joanne M. Pascarella et al.

Issued: Jul. 5, 1994

A prosthetic implant for resurfacing a damaged base portion of the proximal phalanx in a human great toe comprises a base fabricated from titanium, ceramic or other durable and rigid biocompatible material. The base is generally elliptical and includes an anatomically-shaped proximal articular surface having an enlarged build-up on the lateral end thereof. The base also includes a generally planar distal seating surface disposed for engaging the sectioned portion of the proximal phalanx. An elongated stem extends distally from the seating surface of the base and includes an array of fins together having a cruciate-shaped cross section. The fins each include a plurality of serrations along their sloping edges for anchoring the stem within the cancellous portion of the proximal phalanx.

U.S. Pat. No. 5,360,450

Inventor: Sandro Giannini

Issued: Nov. 1, 1994

A prosthesis for the correction of a flatfoot condition of a patient, which is designed for insertion inside a recess or tarsal sinus defined between a first bone or astragalus and a second bone or calcaneus; wherein the prosthesis is made of bioreabsorbable material. The prosthesis has a club-shaped body or a slightly conical body.

U.S. Pat. No. 5,458,648

Inventor: James Berman et al.

Issued: Oct. 17, 1995

A nonconstrained, total great toe joint implant for the metatarsophalangeal joint made of a first component with a convex, partially spherical surface ending in a rear surface from which a longitudinally asymmetric implantation stem projects and having a flange on the dorsal side of the implant which extends the convex surface past the rear surface. The rear surface is inclined 10 degrees relative to a normal plane which intersects this surface. The metatarsal bone is resected accordingly. The phalangeal implant component is made of a base with a stem for placement in a bone cavity, projecting from a rear side thereof and having a low-friction, concavely curved insert affixed to the base which slidably engages and cooperates with the convex surface of the metatarsal implant component. The base has an outline corresponding approximately to the outline of the resected surface on the phalangeal bone to eliminate bone-overhang and bony overgrowth that may result from such an overhang and which can compromise the proper functioning of the implant. The metatarsal implant component has right foot and left foot configurations resulting from the relative positioning and orientation of the asymmetrically shaped stem projecting from the rear surface thereof.

U.S. Pat. No. 5,683,466

Inventor: Glenn C. Vitale

Issued: Nov. 4, 1997

The present invention relates to an articular joint replacement system. The system has first and second components. Each component has a tapered head piece for covering the end of a bone and for acting as an articular surface, an integrally formed screw stem having a length sufficient to extend into the medullary canal, and inwardly angled bone grips affixed to the underside of the head piece to allow solid fixation to the bone by compression press fit. The head piece of the first component is provided with a shaped exterior surface which complements the shaped exterior surface of the head piece of the second component and which allows motion in three planes.

U.S. Pat. No. 6,099,571

Inventor: John G. Knapp

Issued: Aug. 8, 2000

An articulated prosthesis includes first and second stem members each anchorable to a bone member at one of the ends of the stem member and the stem member having an aperture with a surrounding surface at the other end. Disposed between the first and second stem members is a movable joint part including a socket and ball combination. The socket has a generally spherical configuration with a hollow interior and a rectangular access port to the interior.

The socket has one surface portion having a complementary configuration to the surrounding surface of the ends of the stem member for adjustable connection to one of the stem members. The ball has a circular configuration with a thickness configured to pass through the access port so that the ball can be rotated within the socket to encapsulate and secure the ball for rotatable motion. The ball has a surface portion having a complementary configuration to the surrounding surface of the stem member ends for adjustable connection to the other stem member. An arcuate extending tab on the ball provides a limiter for rotational and axial movement of the ball within the socket so that the prosthesis imitates the natural movement of a finger or toe.

International Patent Application Number WO 01/03613

Inventor: Elmo Emmanuel

Issued: Jan. 18, 2001

An implant device for providing an othopaedic joint comprises a metatarsal implant (200) having an articular surface (15) and lateral stability rib (16); a phalangeal implant having a tapered cavity and, therebetween, a sliding miniscus having a lateral stability groove (23) which co-operates with rib (16) and a tapered stem which is housed in the tapered cavity of the phalangeal implant (204). The metatarsal implant is arranged to be secured in a proximal bone and the phalangeal implant is arranged to be secured in a distal bone, whereby the phalangeal component is arranged to rotate and be capable of translational movement relative to the metatarsal implant by virtue of co-operation with the sliding miniscus.

French Patent Number FR2733412

Inventor: Jean Michel Huc de Bat

Issued: Oct. 31, 1996

The prosthesis has a phalangeal section (1) formed as a screw (3) covered by a detachable plate (6) threaded into the phalanx. A metatarsal prosthesis (2) is shaped on its left surface and covers an osseous area of the metatarsal. The prostheses have their surfaces shaped to allow mutual contact. The surface of the phalangeal section can be totally planar. The metatarsal prosthesis can be in two parts including a contact zone (8) and a retaining section between the external surface and the lateral wall of the metatarsus.

While these devices may be suitable for the purposes for which they were designed, they would not be as suitable for the purposes of the present invention, as hereinafter described.

SUMMARY OF THE PRESENT INVENTION

The present invention relates generally to implants and, more specifically, to a metatarsal implant comprising a head and neck prosthesis anchored by an implant stem positioned within the remaining portion of the metatarsal bone and further secured by a pair of screws that passes substantially perpendicular through the implant stem at opposing quadrants. The implant further includes a phalanx component anchored to the proximal phalanx bone and engaging the metatarsal implant. The metatarsal implant also includes a cavity for inserting a targeting bracket having a post and cantilevered arm terminating in an annular ring. The targeting bracket allows for blind drilling at least one hole for receipt of the transverse locking screws passing through the implant stem.

A primary object of the present invention is to provide a metatarsal head and neck implant that overcomes the shortcomings of the prior art.

Another object of the present invention is to provide a metatarsal head and neck implant having an implant stem depending therefrom.

Still another object of the present invention is to provide a metatarsal head and neck implant wherein the implant stem is received within the metatarsal bone and secured therein for anchoring the implant to the metatarsal bone.

Another object of the present invention is to provide a metatarsal head and neck implant wherein the implant is anchored by at least one locking screw received by at least one aperture extending transversely through the implant stem.

Yet another object of the present invention is to provide a metatarsal head and neck implant having a cavity for receiving a targeting bracket therein.

A further object of the present invention is to provide a metatarsal head and neck implant wherein the targeting bracket provides means for blind drilling the transverse bore.

Still yet another object of the present invention is to provide a phalanx component having an implant stem depending therefrom providing means for anchoring said implant to a proximal phalanx bone.

Another object of the present invention is to provide a phalanx component for engagement with the metatarsal head and neck implant.

A further object of the present invention is to provide a phalanx component for engagement with the metatarsal head and neck implant wherein the phalanx is anchored to the proximal phalanx bone by an implant stem and a locking screw.

Additional objects of the present invention will appear as the description proceeds.

The present invention overcomes the shortcomings of the prior art by providing a metatarsal implant comprising a head and neck prosthesis anchored by an implant stem positioned within the remaining portion of the metatarsal bone and further secured by a pair of screws that pass substantially perpendicular through the implant stem at opposing quadrants. The present invention also provides a phalanx component anchored to the proximal phalanx bone by a locking screw wherein the phalanx component engages the head of the metatarsal implant.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which:

FIG. 2 is an illustrative comparison view of a prior art implant and the metatarsal implant of the present invention;

DESCRIPTION OF THE REFERENCED NUMERALS

Figure 1:
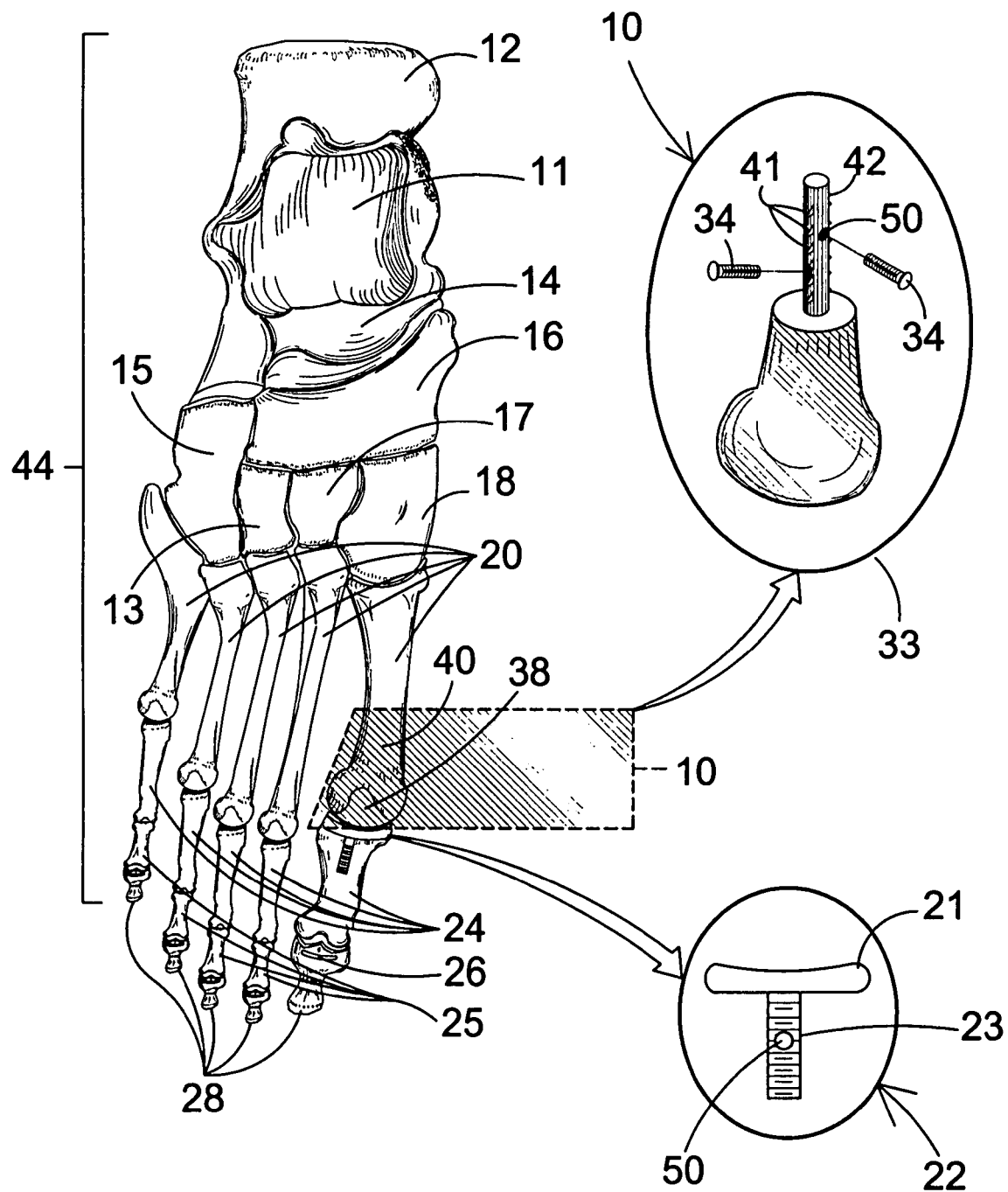
FIG. 1 is an illustrative view of the area of the metatarsal implant of the present invention.

Turning now descriptively to the drawings, in which similar reference characters denote similar elements throughout the several views, the Figures illustrate the metatarsal implant device of the present invention. With regard to the reference numerals used, the following numbering is used throughout the various drawing figures.

10 metatarsal implant
11 tibia bone
12 calcaneous bone
13 cubcid bone
14 talus bone
15 lateral cuneiform bone
16 navicular bone
17 intermediate cuneiform bone
18 medial cuneiform bone
20 metatarsal bone
21 phalanx head
22 phalanx component
23 phalanx stem
24 proximal phalanx bone
26 extensor hallucis longus
28 distal phalanx bone
30 big toe
32 prior art implant
33 circle
34 locking screw
36 targeting recess
38 head of metatarsal implant
40 neck of metatarsal implant
41 saw-toothed ridges
42 implant stem
44 foot
46 drill with drill bit
48 target for drill
49 first drill aperture
50 apertures
52 targeting bracket
54 anchoring member
56 post
58 annular ring
60 second targeting aperture
62 second drill target
63 second drill aperture
64 second locking screw
66 second aperture

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments; practitioners skilled in the art will recognize numerous other embodiments as well. For definition of the complete scope of the invention, the reader is directed to appended claims.

Turning now descriptively to the drawings, in which similar reference characters denote similar elements throughout the several views, FIGS. 1 through 9 illustrate a metatarsal implant device of the present invention which is indicated generally by the reference numeral 10.

An illustrative view of a foot 44 having the metatarsal implant device 10 of the present invention inserted therein is shown illustratively in FIG. 1. All bones are connected to each other and supported by connective tissues including tendons and muscles. These connective tissues are not shown in the Figures as they do not directly relate to the metatarsal implant 10 of the present invention. Additionally, cartilage (not shown) is positioned between bones thereby providing a cushion to prevent direct contact between the ends of one another. Thus, hereinafter it is implied that at least one of tendons, muscles and cartilage are present when connecting a first bone to a second bone.

In the human foot 44, an end of the tibia bone 11 is connected via connective tissue (not shown) to a first end of a talus bone 14. The talus bone 12 is surrounded and supported by the calcaneous bone 12. The talus bone 14 is connected to the navicular bone 16. The navicular bone 16 is connected to each of the lateral cuneiform bone 15, the intermediate cuneiform bone 17 and the medial cuneiform bone 18. The cubcid bone 13 is connected to each of the calcaneous bone 12, the navicular bone 16 and the lateral cuneiform bone 15. Metatarsal bones 20 are connected to each one of the cuneiform bones 15, 17, 18 and the cubcid bone 13. The metatarsal bones 20 are each connected proximal phalanx 24 which is further connected to the middle phalanges 25. With respect to the four smaller toes, the middle phalanges 25 are connected to the distal phalanx 28 thereby forming the toes of the human foot 44. With respect to the big toe, the extensor hallucis longus 26 is connected between the proximal phalanx 24 and the distal phalanx 26. The big toe does not include the middle phalanx 25.

The metatarsal implant 10 of the present invention is comprised of a head 38 and a neck 40 as shown in the shaded portion of FIG. 1 and is shaped substantially similar to the metatarsal bone 20 in which is it being implanted. The metatarsal implant 10 is shown in greater detail within the circle labeled with the reference numeral 33. Extending outward from the neck 40 of the metatarsal implant 10 is an implant stem 42 for insertion into the metatarsal bone 20. The implant stem 42 contains a plurality of apertures 50 for receiving a plurality of locking screws 34 therein. A plurality of threaded locking screws 34 are screwed into the plurality of corresponding apertures 50 for securing the metatarsal implant 10 to the metatarsal bone 20. The shaft of the implant stem 42 also includes saw-toothed edges to further aide in anchoring the implant 10 in the metatarsal bone 20. The implant 10 of the present invention further includes a phalanx component 22 which shown in greater detail in the circle labeled with the same reference numeral. The phalanx component 22 includes a phalanx head 21 having a phalanx stem 23 extending therefrom. The phalanx stem 23 also includes a recess 50 for receiving a locking screw 34 therein. The phalanx stem 23 is implanted into the proximal phalanx bone 24 and secured therein by the locking screw 34. Thus, the phalanx head 21 engages the metatarsal head 38 and prevents further wearing of the bones 20 and 24. Additionally, the patient experiences reduced pain in everyday walking activity.

As shown in FIG. 1 and described in FIGS. 2-9 hereinafter, the metatarsal implant 10 of the present invention is implanted within the metatarsal bone 20 and proximal phalanx 24 of the big toe. However, this is shown for purposes of example only and the implant 10 of the present invention can be inserted in any metatarsal bone 20 and proximal phalanx 24 in the human foot as deemed medically necessary.

FIG. 2 is a comparative illustrative view of a prior art metatarsal implant as shown in FIG. 2A and the metatarsal implant 10 of the present invention as shown in FIG. 2B. As will be described hereinbelow, there implant 10 of the present invention provides advantages not seen or contemplated by the prior art implant as shown in FIG. 2A.

A big toe 30 including the head of the metatarsal implant of the prior art 32 is shown illustratively in FIG. 2A. A prior art metatarsal implant 32 is shown inserted into the metatarsal bone 20. The distal phalanx bone 28 is connected to a first end of the proximal phalanx bone 24. A second end of the proximal phalanx bone 24, opposite the first end, engages the prior art metatarsal implant 32.

FIG. 2B shows a big toe 30 including the metatarsal implant 10 of the present invention Shown is the distal phalanx bone 28 connected to the first end of the proximal phalanx bone 24. The phalanx stem 23 of the phalanx component 22 is inserted into the second end of the proximal phalanx bone 24, opposite of the first end. The head 38 and neck 40 of the metatarsal implant is shown inserted into and secured in the metatarsal bone 20 via an implant stem 42, shown in FIG. 1. The phalanx head 21 of the phalanx component 22 engages the head 38 of the metatarsal implant.

As can be seen the metatarsal implant 10 of the present invention includes the addition of the phalanx component for engaging the head 38 of the metatarsal implant 10. This engagement allows for a more comfortable and natural interaction between the metatarsal bone 20 and the proximal phalanx 20. Additionally, it is clear that the implant 10 of the present invention has greater surface area than prior art implant which have traditionally only replaced the head of the metatarsal bone 20. By anchoring an implant having the head 38 and neck 40 as in the present invention, the structural integrity of the metatarsal bone 20 is maintained.

Figure 3:
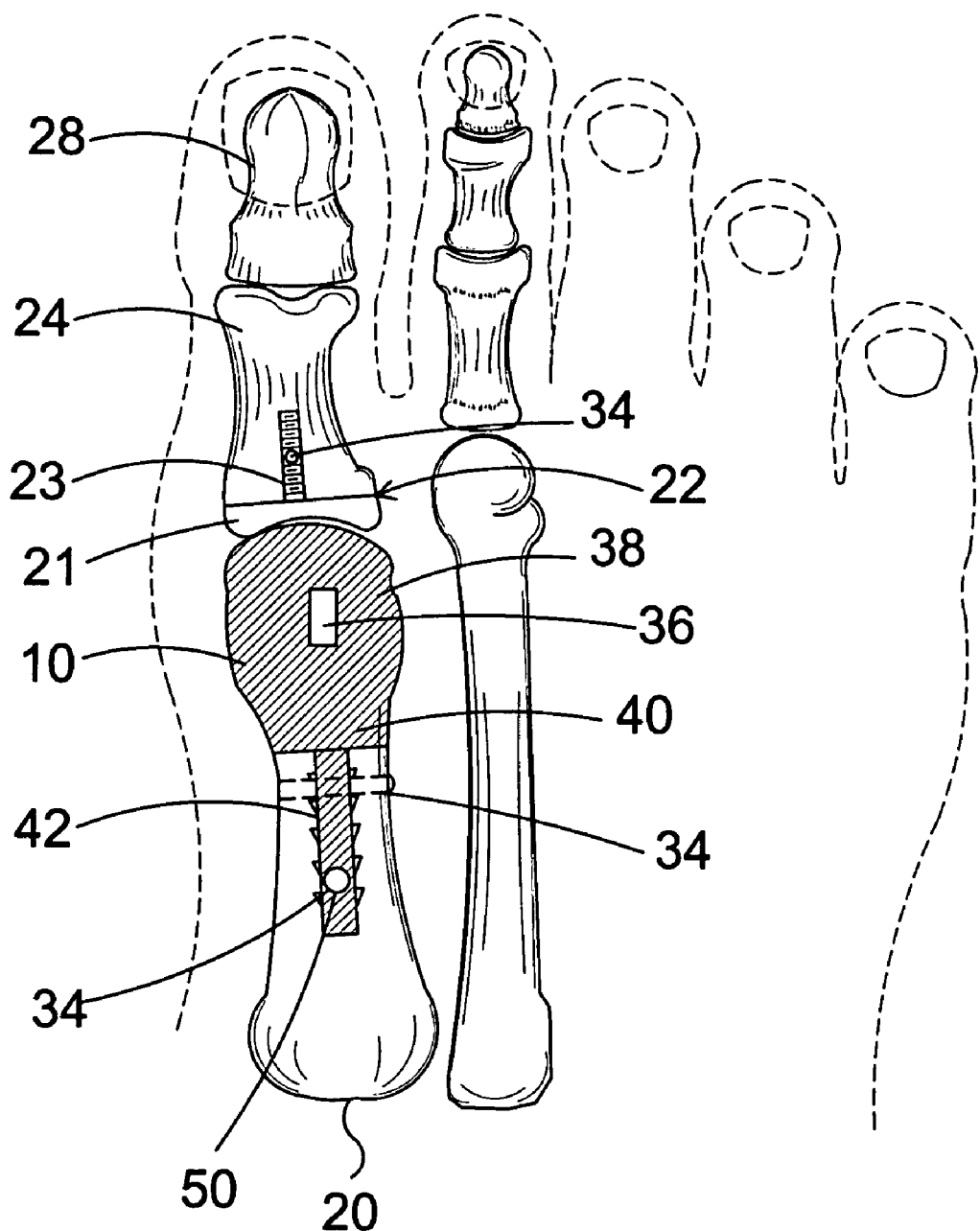
FIG. 3 is an anterior view of the metatarsal implant of the present invention.

FIG. 3 is an anterior view of the present invention. Shown is a top foot view of the metatarsal implant 10 of the present invention having a head 38 and neck 40 prosthesis anchored by an implant stem 42 within the remaining portion of the metatarsal bone and further secured by a screw 34 that is received within the recess 50 and passes substantially perpendicular through the implant stem 42.

As shown herein, the distal phalanx bone 28 is connected to the first end of the proximal phalanx bone 24. The phalanx component 22 having the phalanx head 21 and the phalanx stem 23 extending from the head 21 is anchored in the second end of the proximal phalanx bone 24 via the phalanx stem. The phalanx component 22 is further secured by a threaded locking screw 34 that passes substantially perpendicular through the apertures 50 of the phalanx stem 23 of the phalanx component 22.

The metatarsal implant 10 is comprised of a head 38 and a neck 40. Extending from the neck of the metatarsal implant 40 is the implant stem 42. The implant stem 42 has saw-toothed edges 41 to better anchor the implant stem 42 in the metatarsal bone 20. The implant stem 42 is further secured to the metatarsal bone 20 by the plurality of locking screws 34 that pass substantially perpendicular through apertures 50 in the implant stem 42. Extending partially through the head 38 of the metatarsal implant is a targeting recess 36. The targeting recess 36 allows for a user implanting the implant of the present invention to insert a targeting device 52 for drilling a recess through the metatarsal bone 20 that is aligned with the recess 50 extending through the stem 42. The targeting device 52 and targeting recess 36 will be described hereinafter with specific reference to FIG. 5.

Figure 4:
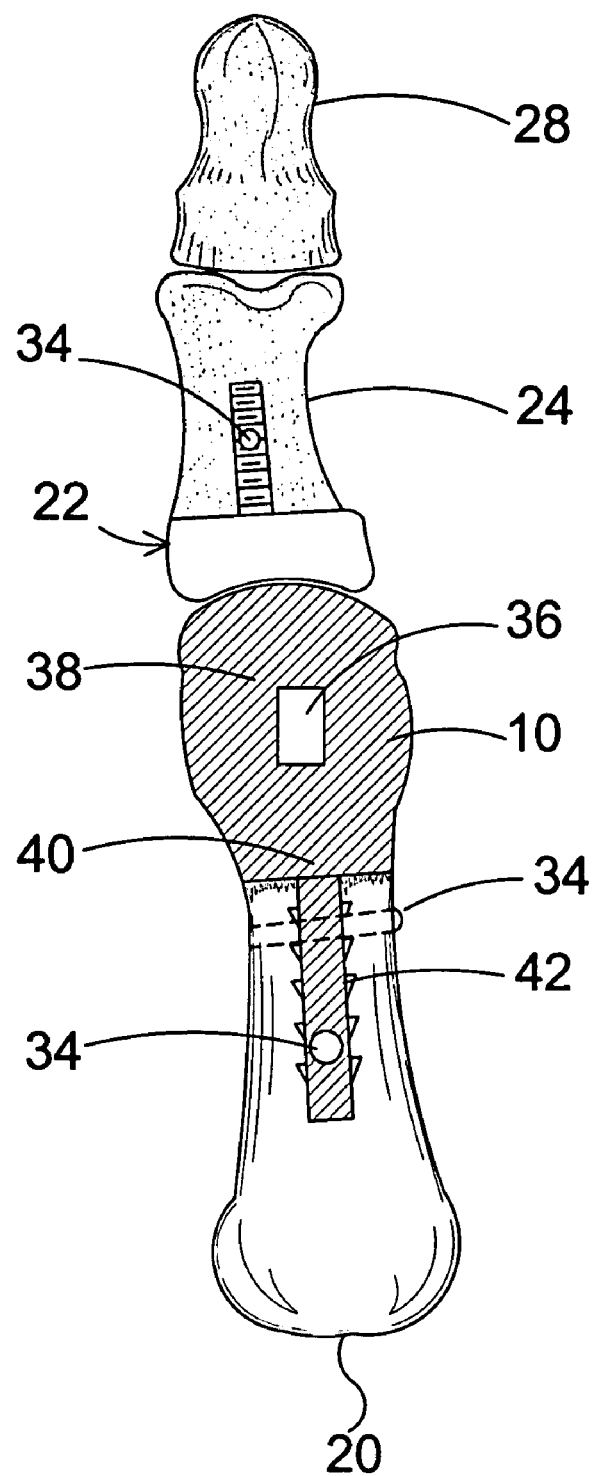
FIG. 4 is a detailed view of the metatarsal implant of the present invention.

FIG. 4 is an illustrative view of the metatarsal implant 10 of the present invention. As shown herein, the distal phalanx bone 28 is connected to the first end of the proximal phalanx bone 24. The phalanx component 22 having the phalanx head 21 and the phalanx stem 23 extending from the head 21 is anchored in the second end of the proximal phalanx bone 24 via the phalanx stem. The phalanx component 22 is further secured by a threaded locking screw 34 that passes substantially perpendicular through the apertures 50 of the phalanx stem 23 of the phalanx component 22.

The metatarsal implant 10 is comprised of a head 38 and a neck 40. Extending from the neck of the metatarsal implant 40 is the implant stem 42. The implant stem 42 has saw-toothed edges 41 to better anchor the implant stem 42 in the metatarsal bone 20. The implant stem 42 is further secured to the metatarsal bone 20 by the plurality of locking screws 34 that pass substantially perpendicular through apertures 50 in the implant stem 42. Extending partially through the head 38 of the metatarsal implant is a targeting recess 36. The targeting recess 36 allows for a user implanting the implant of the present invention to insert a targeting device 52 for drilling a recess through the metatarsal bone 20 that is aligned with the recess 50 extending through the stem 42. The targeting device 52 and targeting recess 36 will be described hereinafter with specific reference to FIG. 5.

Figure 5:
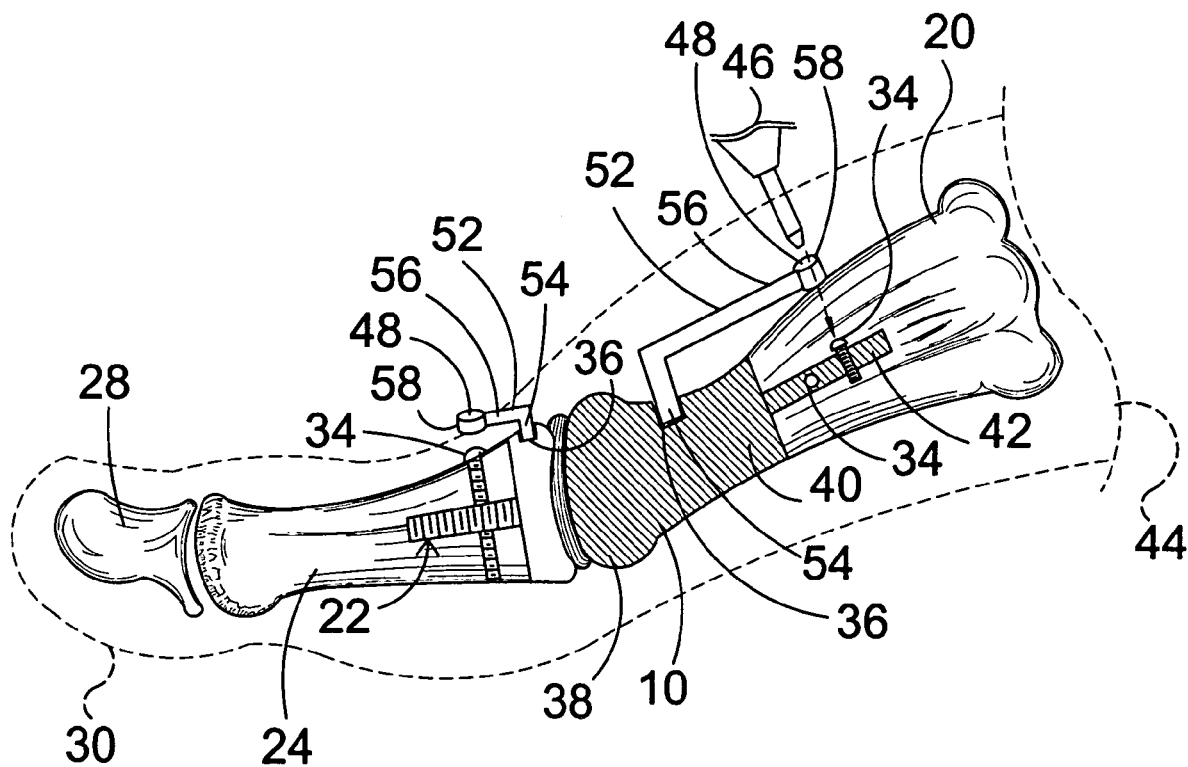
FIG. 5 is a side view of the metatarsal implant of the present invention.

FIG. 5 is a side view of the foot 44 having the metatarsal implant 10 of the present invention. As shown herein, the distal phalanx bone 28 is connected to the first end of the proximal phalanx bone 24. The phalanx component 22 having the phalanx head 21 and the phalanx stem 23 extending from the head 21 is anchored in the second end of the proximal phalanx bone 24 via the phalanx stem. The phalanx component 22 is further secured by a threaded locking screw 34 that passes substantially perpendicular through the apertures 50 of the phalanx stem 23 of the phalanx component 22. Extending partially through the proximal phalanx implant 22 is a targeting recess 36. The targeting recess 36 allows for a user implanting the implant of the present invention to insert a targeting device 52 for drilling a recess through the proximal phalanx bone 24 that is aligned with the recess 50 extending through the stem 23.

Figure 6:
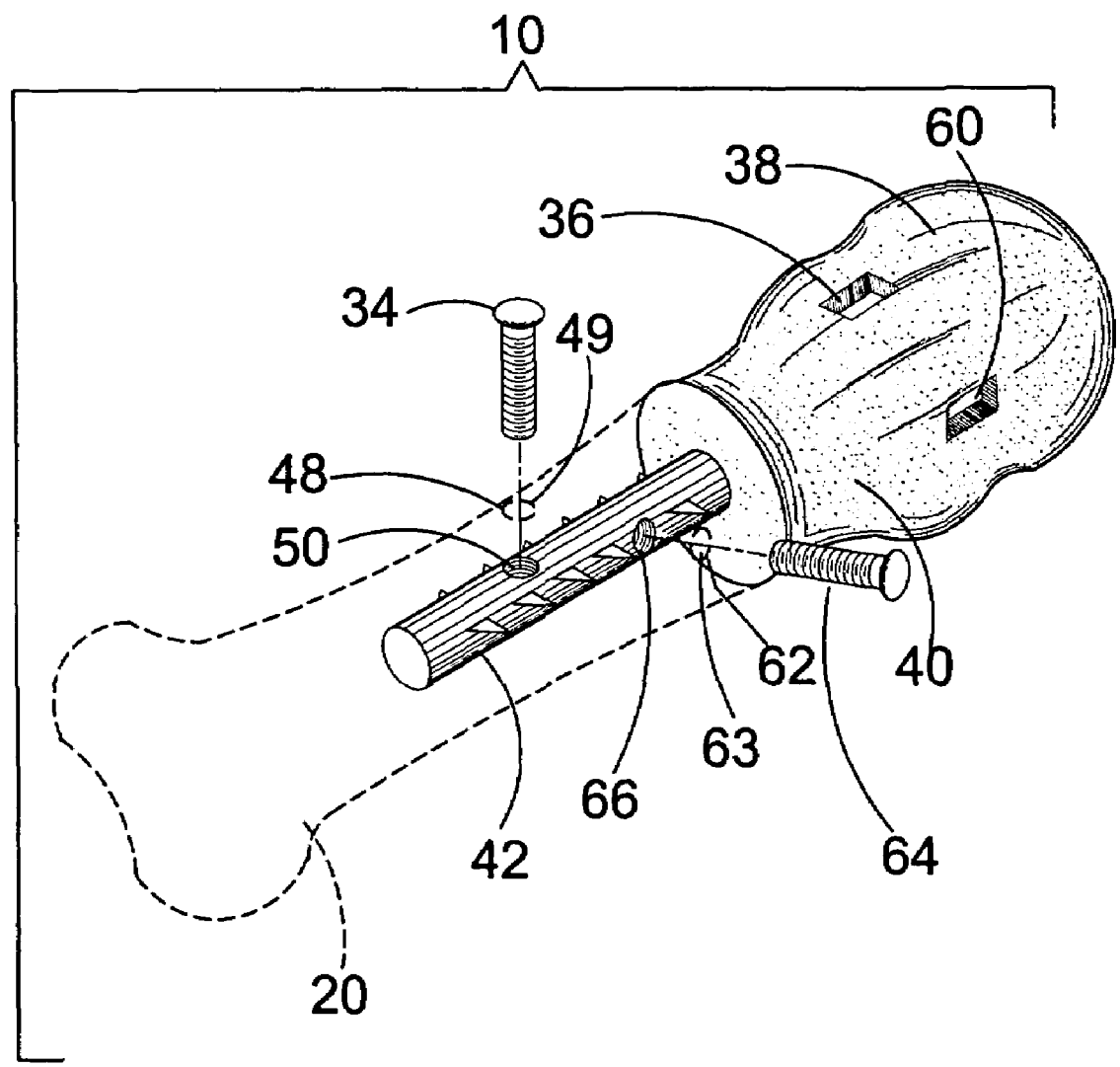
FIG. 6 is a perspective view of the metatarsal implant of the present invention.

The metatarsal implant 10 is comprised of a head 38 and a neck 40. Extending from the neck of the metatarsal implant 40 is the implant stem 42. The implant stem 42 has saw-toothed edges 41 to better anchor the implant stem 42 in the metatarsal bone 20. The implant stem 42 is further secured to the metatarsal bone 20 by the plurality of locking screws 34 that pass substantially perpendicular through apertures 50 in the implant stem 42. Extending partially through the head 38 of the metatarsal implant and/or proximal phalanx implant 22 is a targeting recess 36. The targeting recess 36 allows for a user implanting the implant 10, 22 of the present invention to insert a targeting device 52 for drilling a recess through the metatarsal bone 20 and/or proximal phalanx bone 24 that is aligned with the recess 50 extending through the stem 42. The target bracket 52 is formed from an anchor end 54 having a post 56 connected thereto. An annular ring 58 is connected at a distal end of the post 56. The anchor end of the target bracket 52 is inserted into the targeting recess 36 and annular ring 58 rests on the metatarsal bone 20 and/or proximal phalanx bone 24 thereby creating a target for a drill 46. The targeting bracket 52 is formed rigid so that upon insertion into recess 36, the annular ring 58 is positioned over a point on the metatarsal bone 20 and/or proximal phalanx bone 24 that allows any recess drilled therein to be directly aligned with the recess 50 in the stem 42, 23. Upon drilling the recesses in the metatarsal bone 20 and/or proximal phalanx bone 24, locking screws 34 are received therein. The locking screw further passes through apertures 50 and locks the implant 10, 22 in place FIG. 6 is a perspective view of the metatarsal implant 10 of the present invention. Shown herein, the metatarsal implant 10 contains the head 38 and the neck 40. The implant stem 42 extends from the neck 40 of the metatarsal implant. The implant stem 42 has saw-toothed edges protruding from the outer surface thereof to better anchor the implant stem 42 within the metatarsal bone 20. The targeting recess 36 is positioned on the head 38 of the metatarsal implant. The target bracket 52, shown in FIG. 5 is inserted within the targeting recess and the annular ring 58 creates a drill target 48 on the metatarsal bone 20. Upon drilling into the metatarsal bone 20, a first drill aperture 49 is created and a first locking screw 34 is received within the drill aperture 49 and further received by the first apertures 50 thereby at least partially securing the implant 10 within the metatarsal bone.

It is preferable that the implant 10 is secured within the metatarsal bone 20 by at least two locking screws passing through at least two corresponding apertures in the stem 42. However, to ensure further stability therein, in addition the first aperture 50, a second aperture 66 passes through the stem 42. The first aperture 50 and second aperture 66 extend through the stem 42 in different quadrants from one another and are positioned at different points along a length of the stem 42. Therefore, the head 38 further includes a second targeting recess 60 positioned at a different location than the first targeting recess 36. This second targeting recess is able to receive a second targeting bracket therein. The second targeting bracket is formed similarly to the first targeting bracket except it is formed in a different size such that upon receipt within the second targeting recess 60, the annular ring of the second targeting bracket rests on the metatarsal bone 20 at a location different from the annular ring 58 of the first targeting bracket 52 and creates a second drill target 62. Upon drilling through the bone at the second drill target 62, a second drill aperture 63 results. The second drill aperture 63 is aligned with a second recess 66 and is able to receive a second locking screw 64 therein.

Figure 7:
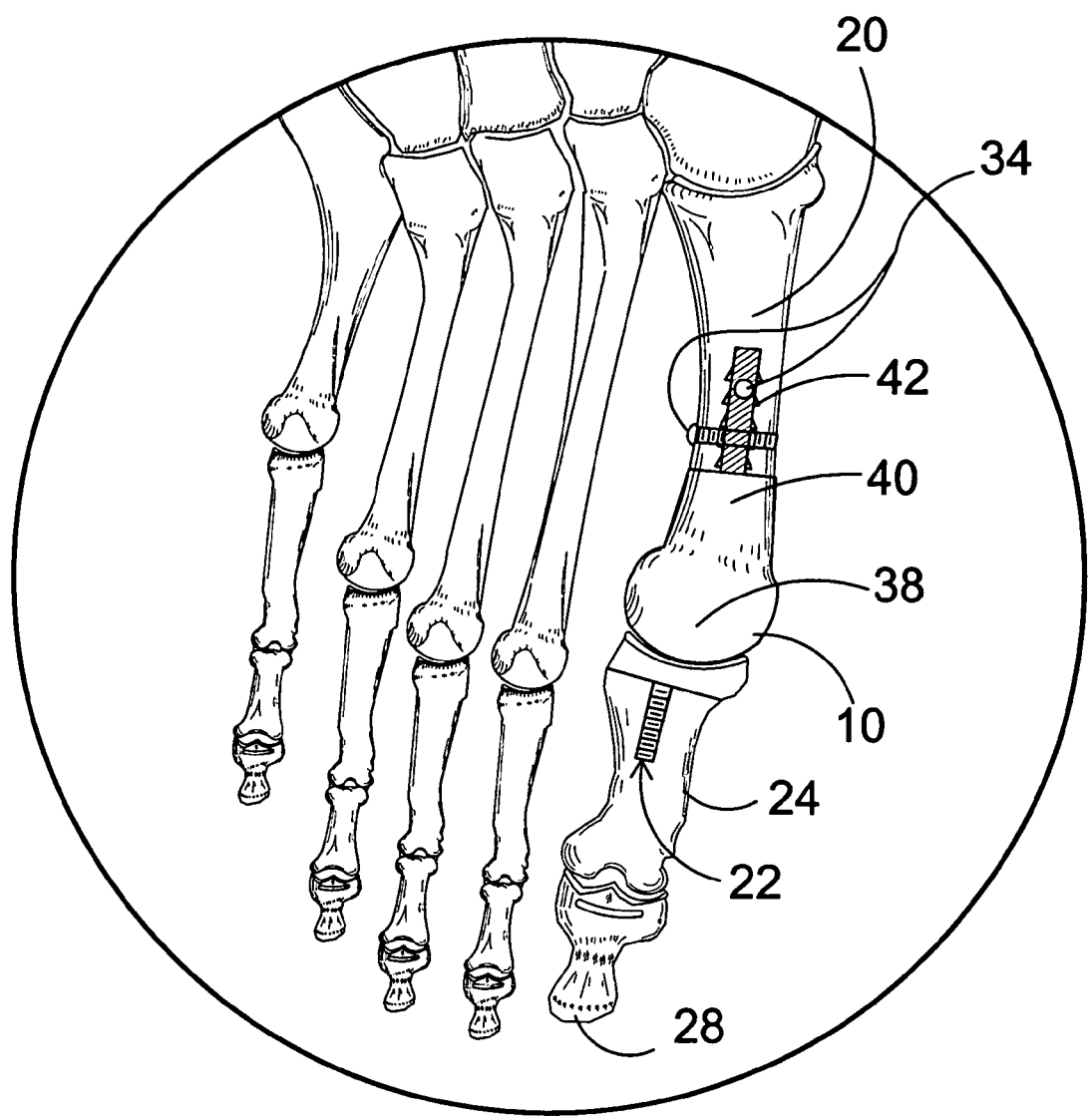
FIG. 7 is a detailed view of the metatarsal implant of the present invention.

FIG. 7 is a detailed view of the metatarsal implant 10 of the present invention. Shown is a top foot view of the metatarsal implant 10 of the present invention having a head 38 and neck 40 prosthesis anchored by an implant stem 42 within the remaining portion of the metatarsal bone and further secured by a screw 34 that is received within the recess 50 and passes substantially perpendicular through the implant stem 42.

As shown herein, the distal phalanx bone 28 is connected to the first end of the proximal phalanx bone 24. The phalanx component 22 having the phalanx head 21 and the phalanx stem 23 extending from the head 21 is anchored in the second end of the proximal phalanx bone 24 via the phalanx stem. The phalanx component 22 is further secured by a threaded locking screw 34 that passes substantially perpendicular through the apertures 50 of the phalanx stem 23 of the phalanx component 22.

The metatarsal implant 10 is comprised of a head 38 and a neck 40. Extending from the neck of the metatarsal implant 40 is the implant stem 42. The implant stem 42 has saw-toothed edges 41 to better anchor the implant stem 42 in the metatarsal bone 20. The implant stem 42 is further secured to the metatarsal bone 20 by the plurality of locking screws 34 that pass substantially perpendicular through apertures 50 in the implant stem 42. Extending partially through the head 38 of the metatarsal implant is a targeting recess 36. The targeting recess 36 allows for a user implanting the implant of the present invention to insert a targeting device 52 for drilling a recess through the metatarsal bone 20 that is aligned with the recess 50 extending through the stem 42. The targeting device 52 and targeting recess 36 will be described hereinafter with specific reference to FIG. 5.

Figure 8:
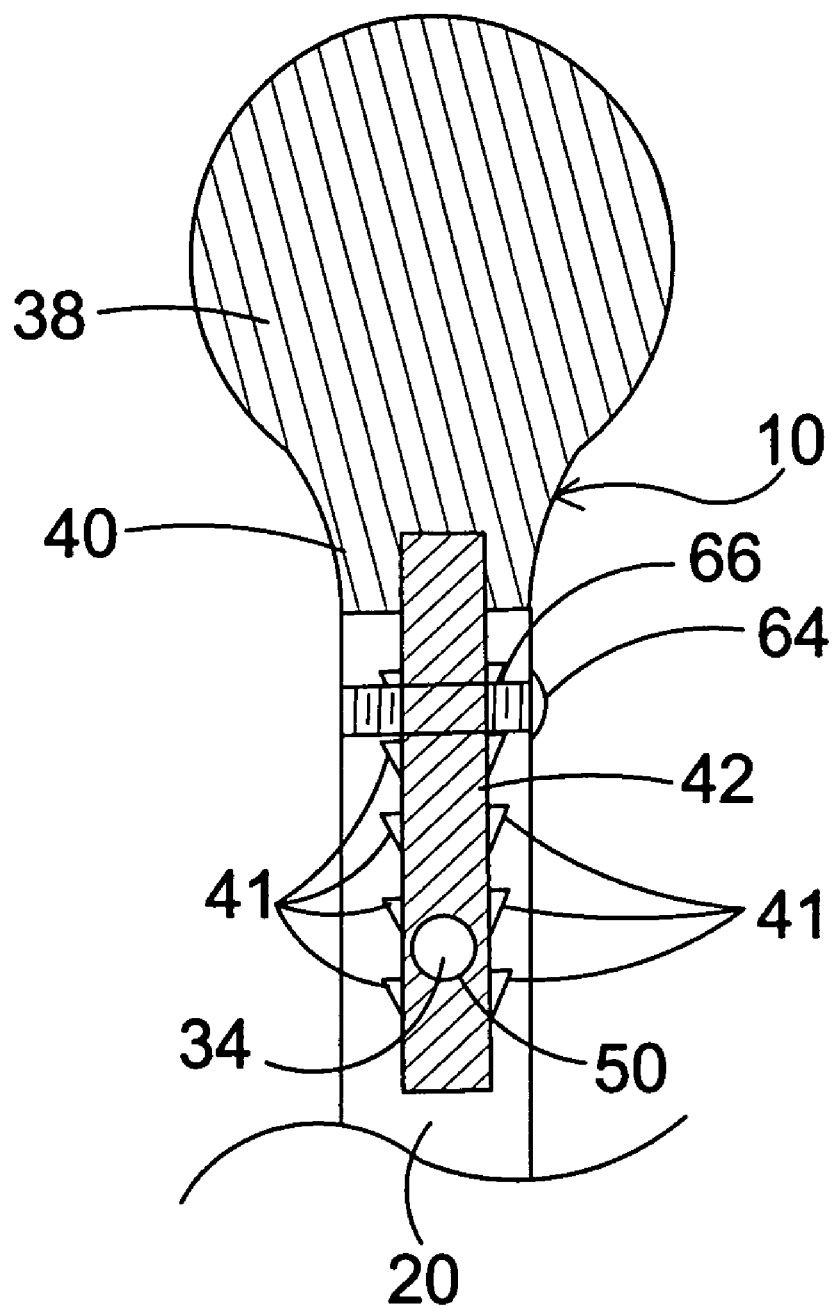
FIG. 8 is a cross sectional view of the metatarsal implant of the present invention.

FIG. 8 is a cross sectional view of the metatarsal head and neck implant of the present invention. Shown herein is the metatarsal implant 10 of the present invention. The metatarsal implant 10 includes the head 38 and the neck 40. Extending from the neck of the metatarsal implant 40 is the implant stem 42. Implant stem 42 has saw-toothed edges 41 to better anchor the implant stem 42 within the metatarsal bone 20. The implant stem 42 is further secured by a first locking screw 34 and a second locking screw 66 that pass substantially perpendicular through a first aperture 50 and a second aperture 66, respectively, in the implant stem 42.

Figure 9:
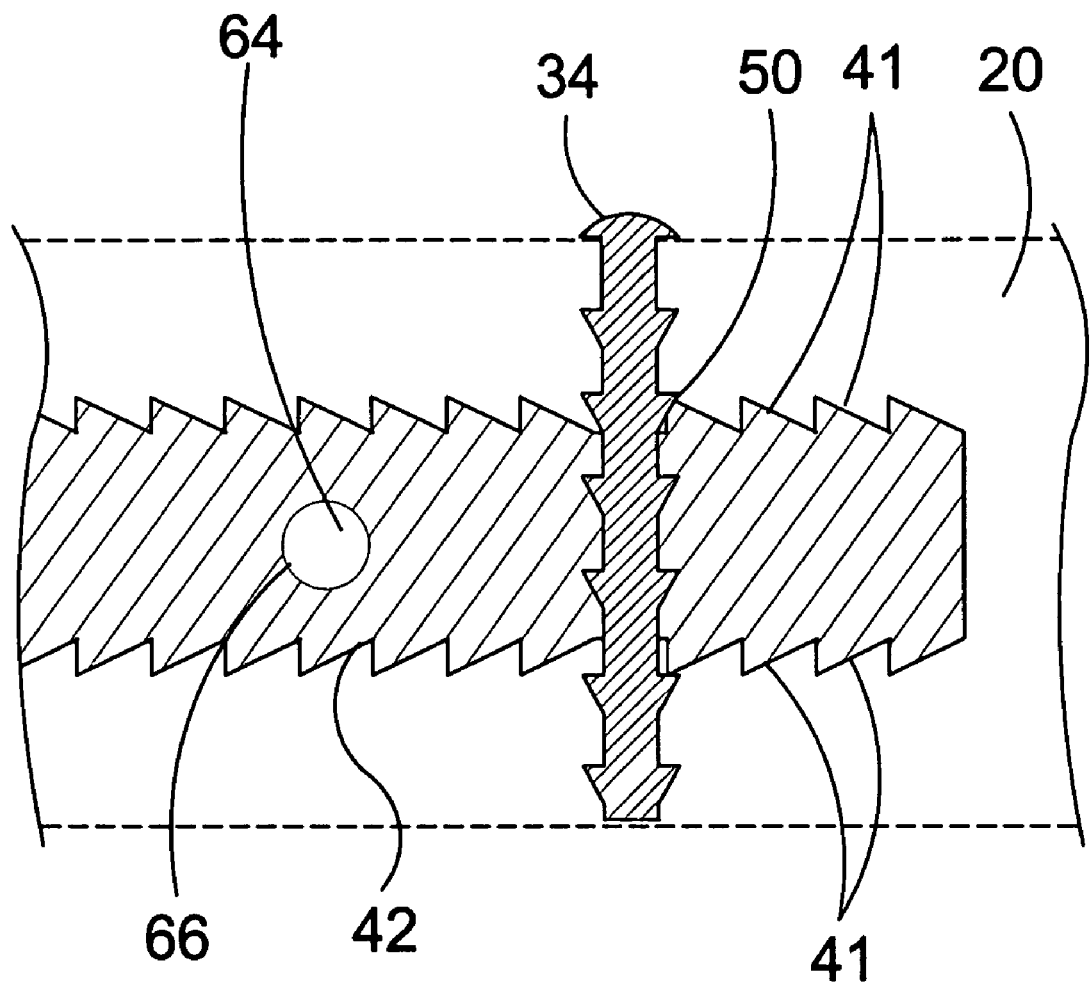
FIG. 9 is an enlarged sectional view of the implant stem of the metatarsal implant of the present invention.

FIG. 9 is an enlarged sectional view of the implant stem of the present invention. Shown herein is the implant stem 42 of the metatarsal implant device 10 of the present invention imbedded in the metatarsal bone 20. Implant stem 42 has saw-toothed edges 41 on the outer surface thereof to better anchor the implant stem 42 in the metatarsal bone 20. The implant stem 42 is further secured by a first locking screw 34 and a second locking screw 66 that pass substantially perpendicular through a first aperture 50 and a second aperture 66, respectively, in the implant stem 42. The first aperture 50 and second aperture 66 are located at different positions along the length of the stem 42. Additionally, the first aperture 50 and second aperture 66 extend though the stem 42 in different quadrants from one another and the throughbores created by each of the apertures 50, 66 result in two apertures that are perpendicular to one another. This design allows for the implant 10 to be more securely anchored within the metatarsal bone 20.

It will be understood that each of the elements described above, or two or more together may also find a useful application in other types of devices differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

The invention claimed is:

1. A prosthetic metatarsal implant comprising:
   a. a head and a neck extending from said head;
   b. a first stem having a first anchoring aperture extending transversely therethrough extending from said neck for insertion into a metatarsal bone;
   c. means comprising a locking screw received by said first aperture for anchoring said first stem in said metatarsal bone;
   d. a first targeting recess extending only partially through at least one of said head and said neck of said implant;
   e. a first targeting bracket comprising a first L-shaped member having a distal end of one leg mounted in and totally enclosed within said first targeting recess and an annular ring mounted on a distal end of a second leg of said first L-shaped member for aligning a drill bit with said anchoring aperture in said stem in said metatarsal bone;
   f. a phalanx component having a phalanx head and phalanx stem extending therefrom for insertion and anchoring in a proximal phalanx bone;
   g. said phalanx stem having an anchoring aperture extending transversely therethrough;
   h. a targeting recess extending only partially through said phalanx head;
   i. a second targeting bracket comprising a second L-shaped member having a distal end of one leg of said second L-shaped member mounted in and totally enclosed within said phalanx targeting recess and an annular ring mounted on a distal end of a second leg of said second L-shaped member for aligning a drill bit with said anchoring aperture in said phalanx stem in said proximal phalanx bone; and
   j. means comprising a locking screw received by said anchoring aperture in said phalanx stem for anchoring said phalanx stem in said proximal phalanx bone.

2. The implant as recited in claim 1, wherein said first stem has a saw tooth configuration on outer surfaces thereof for further securing said stem within said metatarsal and proximal phalanx bones.

3. The implant as recited in claim 1, in which said first stem has a second anchoring aperture angularly offset from said first anchoring aperture, there being a separate targeting recess and targeting bracket for each anchoring aperture.

4. The implant as recited in claim 3, wherein said head and neck are formed from materials that will not irate the human body.

* * * * *